United States Patent [19]
Neely

[11] Patent Number: 6,001,842
[45] Date of Patent: *Dec. 14, 1999

[54] COMPOSITIONS AND METHODS FOR USE IN ISCHEMIA-REPERFUSION AND ENDOTOXIN-RELATED TISSUE INJURY

[75] Inventor: Constance F. Neely, Raleigh, N.C.

[73] Assignee: Trustees of the University of Pennsylvania, Philadelphia, Pa.

[*] Notice: This patent is subject to a terminal disclaimer.

[21] Appl. No.: 09/004,938

[22] Filed: Jan. 9, 1998

Related U.S. Application Data

[63] Continuation-in-part of application No. 08/716,192, Sep. 30, 1996, Pat. No. 5,733,916.
[51] Int. Cl.[6] .................... A61K 31/52; A61K 31/505; A61K 31/515
[52] U.S. Cl. ................ 514/263; 514/266; 514/262; 514/261; 514/267; 514/352; 514/271; 514/272
[58] Field of Search ....................... 514/263, 266, 514/262, 261, 267, 352, 271, 272

[56] References Cited

U.S. PATENT DOCUMENTS

| | | | |
|---|---|---|---|
| 4,772,607 | 9/1988 | Badger et al. | 514/263 |
| 4,783,530 | 11/1988 | Rzeszotarski et al. | 544/267 |
| 4,968,672 | 11/1990 | Jacobson et al. | 514/46 |
| 5,032,593 | 7/1991 | Rzeszotarski et al. | 514/263 |
| 5,175,290 | 12/1992 | Rzeszotarski et al. | 544/267 |
| 5,248,678 | 9/1993 | Costa et al. | 514/220 |
| 5,366,977 | 11/1994 | Pollard et al. | 514/263 |
| 5,504,090 | 4/1996 | Neely | 514/263 |
| 5,733,916 | 3/1998 | Neely | 514/262 |
| 5,773,306 | 6/1998 | Neely | 436/518 |
| 5,786,360 | 7/1998 | Neely | 514/263 |

OTHER PUBLICATIONS

Adkins et al., "Adenosine Prevents PMA–induced Lung Injury Via an A2 Receptor Mechanism" *Appl. Physiol.*, 1993, 74(3):982–988.

Abbracchio MP and Burnstock G, "Purinoceptors: Are There Families of P2X and P2Y Purinoceptors?" *Pharmac. Ther.* 64:445–475, 1994.

Arai M, et al., "An experimental study on the severe type of alcoholic liver disease—a pathogenetic role of potentiated activation of complement system of endotoxin after chronic ethanol consumption", *Jap. J. Gastroenterology* 86:1089–1095, 1989.

Abel–Aziz MT et al., "Role of Endotoxin in Liver Injury", *J. Clin. Biochem. Nutr.* 22:19–29, 1997.

Adkins et al., "Adenosine Prevents PMA–induced Lung Injury Via an A2 Receptor Mechanism", *Appl. Physiol.* 74(3):982–988, 1993.

Behar, Cohen FF, et al., "Iontophoresis of Dexamenthasone in the Treatment of Endotoxin–Induced–Uvetis in Rats", *Exp. Eye Res.* 65:533–545, 1997.

Bo, X. and Burnstock, G., "Heterogeneous Distribution of $^{3}H\alpha,\beta$–Methylene ATP Binding Sites in Blood Vessels" *J. Vas. Res.* 30:87–101, 1993.

Berger D, et al., "Determination of Endotoxin–Neutralizing Capacity of Plasma in Postsurgical Patients", *E. Surg. Res.* 28:130–139, 1996.

Bultmann R. et al., "$P_2$–purinoceptor antagonists: I. Blockade of $P_2$–purinoceptor subtypes and ecto–nucleotidases by small aromatic isothiocyanato–sulphonates", *Naunyn–Schmied. Arch. Pharmacol.* 354:481–490, 1996.

Bultmann R, et al. "$P_2$–purinoceptor anatagonists: III. Blockade by $P_2$–purinoceptor subtypes and ecto–nucleotidases by compounds related to suramin", *Naunyn–Schmied. Arch. Pharmacol.* 354:498–504, 1996.

Burnstock G, "Cholinergic and Purinergic Regulation of Blood Vessels" *Handbook of Physiology—The Cardiovascular System II*, 2nd Edition, vol. 2, Chapter 19, pp. 567–612, 1979.

Burnstock, G. and Kennedy, C., "Is There A Basis For Distinguishing Two Types of $P_2$–Purinoceptor?" *Gen. Pharmac.* 16:433–440, 1985.

Burnstock, G. and Warland, J.J.I., "$P_2$–purinoceptors of two subtypes in the rabbit mesenteric artery: reactive blue 2 selectively inhibits responses mediated via the $P_{2y}$– but not the $P_{2x}$–purinoceptor" *Br. J. Pharmacol.* 90:383–391, 1987.

Berti et al., "Pharmacological Activity of Bamifylline On Lung Anaphylaxis: In Vitro Studies", *Pharmacol. Res.* 22:143–150, 1990.

Berti et al. "New Pharmacological Data on the Bronchospasmolytic Activity of Bamifylline", *Arzneum Forsch/Drug Res.* 38:40–44, 1988.

Cronstein BN, et al., "Adenosine Modulates the Generation of Superoxide Anion by Stimulated Human Neutrophils via Interaction with a Specific Cell Surface Receptor" *Ann NY Acad Sci* 451:291–301, 1985.

Drury AN, Szent–Gyorgi A, "The Physiological Activity of Adenine Compounds[1] with Especial Reference To Their Action Upon The Mammalian Heart", *J. Physiol (Lond)* 68:213–237, 1929.

Duffy LC, et al. "Concordance of bacterial Cultures with Endotoxin and Interleukin–6 inNecrotizing Enterocolitis", *Digestive Dis. and Sci.* 42:359–365, 1997.

Egan TM, et al., "Lung transplantation", *Curr Probl Surg* 26:675–751, 1989.

Ely, SW et al., "Functional and Metabolic Evidence of Enhanced Myocardial Tolerance to Ischemia and Reperfusion with Adenosine" *J. Thorac Cardiovasc Surg* 90:549–556, 1985.

(List continued on next page.)

*Primary Examiner*—Deborah C. Lambkin
*Attorney, Agent, or Firm*—Law Offices of Jane Massey Licata

[57] ABSTRACT

Methods of preventing or treating ischemia-reperfusion injury in an organ by administration of a composition containing a selective $A_1$ adenosine receptor antagonist and/or a $P_{2x}$ purinoceptor antagonist are provided. Methods of preventing or treating endotoxin-related tissue injury by administration of a composition containing a selective $A_1$ adenosine receptor antagonist and/or a $P_{2x}$ purinoceptor antagonist are also provided.

6 Claims, No Drawings

OTHER PUBLICATIONS

Ely SW, Berne RM, "Protective Effects of Adenosine in Myocardial Ischemia" *Circ* 85:893–904, 1992.

Goddard CM, et al., "Myocardial morphometric changes related to decreased contractility after endotoxin", *Am. J. Physiol.* 270:H1446–H1452, 1996.

Hazan Y, et al., "The diagnostic value of amniotic fluid Gram stain examination and limulus amebocyte lysate assay in patients with preterm birth", *Acta Obstet. Gynecol. Scand.* 74:275–280, 1995.

Hurley JC and Tosolini FA, "A quantitative micro–assay for endotoxin and correlation with baterial density in urine", *J. Microbiol. Methods* 16:91–99, 1992.

Haselton FR et al., "Adenosine Decreases Permeability of In Vitro Endothelial Monolayers", *J Appl Physiol* 74:1581–1590, 1993.

Herbert JM, et al. "Hypoxia Primes Endotoxin–Induced Tissue Factor Expression in Human Monocytes and Endothelial Cells by a PAF–Dependent Mechanism", *J. Cellular Physiol.* 169:290–299, 1996.

Hopwood, A.M. and Burnstock, G., "ATP mediates coronary vasoconstriction via $P_{2x}$–purinoceptors and coronary vasodilation via $P_{2y}$–purinoceptors in the isloated perfused rat heart", *E. J. Pharmacol.* 136:49–54, 1987.

Hamvas A, et al., "Inflammation and Oxygen Free Radical Formation During Pulmonary Ischemia–reperfusion Injury", *J Appl Physiol* 72:621–628, 1992.

Humphrey PPA, et al., "New insights on $P^{2x}$ purinoceptors", *Naunyn–Schmied. Arch. Pharmacol.* 352:585–596, 1995.

Houston et al. "Different $P_2$–Purinergic Receptor Subtypes of Endothelium and Smooth Muscle in Canine Blood Vessels", *J. Pharmacol. Exp. Ther.* 241:501–506, 1987.

Hourani SMO, Cusack NJ, *Actions and Structure Activity Relationships of Purines on Platelets. In Purines. Pharmacology and Physiological Roles.* Edited by TW Stone, VCH, London, pp. 163–173, 1985.

Hoyle, C.H.V., "Pharmacological Activity of Adenine Dinucleotides in the Periphery: Possible Receptor Classes and Transmitter Function", *Gen. Pharmac.* 21:827–831, 1990.

Hoyle, C.H.V., "Isolated human bladder: evidence for an adenine dinucleotide acting on $P_{2x}$–purinoceptors and for purinergic transmission", *E. J. Pharmacol.* 174:115–118, 1989.

Ishazaki M, et al., "Usefulness of the Endotoxin Test for Assessing CAPD Peritonitis by Gram–Negative Organisms", *Advances in Peritoneal Dialysis* 12:199–202, 1996.

Janier, MF, et al., "Adenosine Protects Ischemic and Reperfused Myocardium by Receptor–Mediated Mechanisms", *Am J Physiol* 264:H163–H170, 1993.

Kellett, R. et al., "Amelioration of Glycerol–Induced Acute Renal Failure in the Rat with 8–cyclopentyl–1, 3–dipropy–lxanthine", *Br. J. Pharmacol.*, 98:1066–1074, 1989.

Knight, R.J., et al., "Effect of the Selective $A_1$ Adenosine Antagonist 8–cyclopentyl–1, 3–dipropylxanthine on Acute Renal Dysfunction Induced by *Escherichia coli* Endotoxin in Rats", *J. Pharm. Pharmacol.*, 45:979–984, 1993.

Kuratani T, et al., "Experimental Study in a Rabbit Model of Ischemia–reperfusion Lung Injury During Cardiopulmonary Bypass", *J Thorac Cardiovas Surg* 103:564–568, 1992.

Lasley, RD, et al., "Adenosine Improves Recovery of Postischemic Myocardial Function Via an Adenosine $A_1$ Receptor Mechanism", *Am J Physiol* 263:H1460–H1465, 1992.

Liu et al. "Characterization and Disbrituon of $P_2$–Purinoceptor Subtypes in Rat Pulmonary Vessels", *J. Pharmacol. Exp. Ther.* 251:1204–1210, 1989.

Lui GS, et al., "Protection Against Infarction Afforded by Preconditioning is Mediated by $A_1$ Adenosine Receptors in Rabbit Heart", *Circ* 84:350–356, 1991.

Lew WY, et al., "Lipopolysaccharide induces cell shrinkage in rabbit ventricular cardiac myocytes", *Am. J. Physiol.* 272:H2989–H2993, 1997.

Lambrecht et al., "PPADS, a novel functionally selective antagonist of $P_2$ purinoceptor–mediated responses", *E. J. Pharmacol.* 217:217–219, 1992.

Levinson RM, et al., "Reperfusion Pulmonary Edema After Pulmonary Artery Thromboendarterectomy", *Am Rev Resp Dis* 134:1241–1245, 1986.

Liu, P, et al., "Priming of Phagocytes for Reactive Oxygen Production During Hepatic Ischemia–Reperfusion Potentiates the Susceptibility for Endotoxin–Induced Liver Injury", *Circ. Shock* 43:9–17, 1994.

Mayeux PR, "Pathobiology of Lipopolysaccharide", *J. Tox. and Environ. Health* 51:415–435, 1997.

Michel O, et al., "Severity of Asthma Is Related to Endotoxin in House Dust", *Am. J. Resp. Crit. Care Med.* 154:1641–1646, 1996.

McKenna TM, "Prolonged Exposure of Rat Aorta to Low Levels of Endotoxin in Vitro Results in Impaired Contractility", *J. Clin. Invest.* 86:160–168, 1990.

MacKenzie et al. "Comparative study of the actions of $AP_5A$ and $\alpha,\beta$–methylene ATP on nonadrenergic, noncholinergic neurogenic excitation in the guinea–pig vas deferens", *Br. J. Pharmacol.* 94:699–706, 1988.

Murata T, et al., "Reperfusion after a Two–Hour Period of Pulmonary Artery Occlusion Causes Pulmonary Necrosis", *Am Rev Resp Dis* 146:1048–1053, 1992.

Nagata Y and Shirakawa K, "Setting standards for the level of endotoxin in the embryo culture media of human in vitro fertilization and embryo transfer", *Fertility and Sterility* 65:614–619, 1996.

Neely CF, et al., "Adenosine Does Not Mediate the Pulmonary Vasodilator Response of Adenosine 5'–triphosphate in the Feline Pulmonary Vascular Bed", *J. Pharmacol Exp Ther* 250(1):170–176, 1989.

Neely et al., "Adenosine and ATP Produce Vasoconstriction in the Feline Pulmonary Vascular Bed by Different Mechanisms", *J. Pharmacol. and Exp. Therap.*, 258(3):753–761, 1991.

Olafsson B, et al. "Reduction of Reperfusion Injury in the Canine Preparation by Intracoronary Adenosine: Importance of the Endothelium and the No–Reflow Phenomenon", *Circ* 76:1135–1145, 1987.

Ralevic et al. "Characterization of $P_{2x}$– and $P_{2y}$–purinoceptors in the rabbit hepatic arterial vasculature", *Br. J. Pharmacol.* 103:1108–1113, 1991.

Schmeling DJ, et al., "Evidence for Neutrophil–related Acute Lung Injury After Intestinal Ischemia–repurfusion", *Surg* 106:195–201, 1989.

Stone, T.W., "Actions of Adenine Dinucleotides on the Vas Deferens, Guinea–Pig Taenia Caeci and Bladder", *E. J. Pharmacol.* 75:93–102, 1981.

Suzuki, F., et al., "Adenosine $A_1$ Antagonists. 2. Structure––Activity Relationships on Diuretic Activities and Protective Effects against Acute Renal Failure", *J. Med Chem*, 35:3066–3075, 1992.

Sakagami T, et al., "The Endotoxin of Helicobacter pylori Is a Modulator of Host–Dependent Gastritis", Infection and Immunity 65:3310–3316, 1997.

Sugiura Y, et al., "The Herbal Medicine, Sairei–to, Prevents Endotoxin–induced Otitis Media with Effusion in ghe Guinea Pig", *Acta Otolaryngol.* 531:21–33, 1997.

Thornton JD, et al., "Intravenous Pretreatment With $A_1$–Selective Adenosine Analogues Protects the Heart Against Infarction", *Circ* 85:659–665, 1992.

Thornton JD, "Effect of Adenosine Receptor Blockade: Preventing Protective Preconditioning Depends on Time of Initiation", *Am J Physiol* 265:H504–508, 1993.

Toombs CF, et al., "Myocardial Protective Effects of Adenosine Infract Size Reduction With Pretreatment and Continued Receptor Stimulation During Ischemia", *Circ* 86:986–994, 1992.

Unno N, et al., "Inhibition of Inducible Nitric Oxide Synthse Ameliorates Endotoxin–Induced Gut Mucosal Barrier Dysfunction in Rats", *Gastroenterology* 113:1246–1257, 1997.

Vogt BA, et al., "Acquired resistance to acutet oxidative stress. Possible role of heme oxygenase and ferritin", *Lab. Invest.* 72:474–483, 1995.

Vos TA, et al., "Differential Effects of Nitric Oxide Synthase Inhibitors on Endotoxin–Induced Liver Damage in Rats", *Gastroenterology* 113:1323–1333, 1997.

Zamora CA, et al., "Thromboxane Contributes to Pulmonary Hypertension in Ischemia–reperfusion Lung Injury", *J Appl Physiol* 74:224–229, 1993.

Zhao, ZQ, et al. "Receptor–Mediated Cardioprotective Effects of Endogenous Adenosine Are Exerted Primarily During Reperfusion After Coronary Occlusion in the Rabbit", *Circ.* 88:709–719, 1993.

6,001,842

COMPOSITIONS AND METHODS FOR USE IN ISCHEMIA-REPERFUSION AND ENDOTOXIN-RELATED TISSUE INJURY

This application is a CIP of Ser. No. 08/716,192 Sep. 30, 1996, U.S. Pat. No. 5,733,916.

FIELD OF INVENTION

Ischemia followed by reperfusion in an organ produces structural and functional abnormalities in the tissue of that organ and others. Neutrophil infiltration, hemorrhage, edema and necrosis are all observed in tissues following an ischemia-reperfusion injury. $A_1$ and $A_2$ adenosine receptors play an important role in the mechanisms behind these injuries. $P_{2X}$ receptor activation also contributes to an increase in pulmonary vascular tone and pulmonary edema formation following ischemia-reperfusion injury. In the present invention a method is provided which prevents and treats ischemia-reperfusion related organ injury. It has now been found that administration of compositions comprising selective $A_1$ adenosine receptor antagonists and/or $P_{2X}$ receptor antagonists can prevent injuries related to ischemia followed by reperfusion in an organ. Compositions of the present invention can be administered prior to, during or following harvesting a donor organ which will be transplanted, prior to or during a surgical procedure in which ischemia is expected, prior to angioplasty or thrombolytic therapy, or after transplantation or reperfusion of an ischemic organ following surgery, angioplasty or thrombolytic therapy. These compositions can also be used to prevent or treat ischemia-reperfusion injury in high risk patients. These compositions are also useful in preventing endotoxin induced tissue injury.

BACKGROUND OF INVENTION

Nucleotides and nucleosides and their purinoceptors have been found to be important mediators in determining pulmonary vascular (PV) tone. Nucleotides are autacoids; that is, they are released locally, metabolized locally by stereoselective nucleotidases, and act on their own local receptors to bring about changes in vascular tone, and neutrophil and platelet function. The effects of nucleotides and nucleosides on PV tone were first described in 1929 by Drury and Szent-Gyorgi when they demonstrated that the nucleoside adenosine produced a fall in arterial pressure and a rise in pulmonary artery pressure in dogs and cats. Drury A N, Szent-Gyorgi A, *J. Physiol (Lond)* 68:213–237, 1929. Since this discovery, much research has been performed to characterize the role of adenosine and its specific purinoceptors.

Based on pharmacological analysis in isolated systemic vessels, Burnstock originated the purinergic receptor hypothesis. Burnstock G, *Handbook of Physiology-The Cardiovascular System II*, 2nd Edition, Volume 2, Chapter 19, pp 567–612, 1979. Adenosine-sensitive receptors, referred to as $P_1$ receptors, were characterized as having an agonist potency in the order of adenosine >AM >ADP>ATP. These receptors were found to act via an adenylate cyclase system and were antagonized by methylxanthines. Since the original classification was made, $P_1$ receptors have been subdivided into $A_1$ and $A_2$ receptors based upon their effect on adenylate cyclase, receptor affinity and radioligand binding.

$A_1$ receptors inhibit adenylate cyclase activity. High affinity $A_1$ receptors have been identified in brain, heart, lung, kidney, skin, pancreas, stomach, spinal cord, intestines, vas deferens, liver, spleen, testis, adrenergic nerve terminals, white blood cells and fat cells. These receptors preferentially bind the purine moiety of adenosine and the order of potency of adenosine analogues is R-phenylisopropyladenosine (R-PIA)>cyclohexyladenosine (CHA)>5'-N-ethylcarboxamidoadenosine (NECA)=2-chloroadenosine (2-CA)>S-phenylisopropyladenosine (S-PIA).

$A_2$ receptors, on the other hand, stimulate adenylate cyclase activity. Low affinity $A_2$ receptors have been identified in brain, heart, lung, liver, kidney, thymus, spleen, epididymis, vas deferens, adipose tissue, vascular smooth muscle cells, platelets, fibroblasts, lymphocytes, neutrophils and pheochromocytoma cells. They preferentially bind the ribose moiety of adenosine and follow a potency order NECA>2-CA>R-PIA=CHA>S-PIA. $A_2$ receptors have been identified in coronary arteries and 2-phenylaminoadenosine (CV1808) was second only to NECA as the most potent coronary vasodilator.

In the heart, $A_1$ adenosine receptors mediate negative inotropic and negative chronotropic effects while $A_2$ receptors mediate coronary vasodilation. Effects of agonists and antagonists on $A_1$ and $A_2$ adenosine receptors in a variety of tissues have been reported by several different investigators. Bamifylline, a selective $A_1$ adenosine receptor antagonist, has been demonstrated to prevent thromboxane release in the lung, including immunologically sensitized lungs. Berti et al. *Pharmacol. Res.* 22:143–150, 1990; Berti et al. *Arzneum Forsch/Drug Res.* 38:40–44, 1988. Costa et al. (U.S. Pat. No. 5,248,678) disclose a method of treating comatose patients to increase arousal and alertness as measured by the Glascow Coma Score by administering effective amounts of an $A_1$ and/or $A_2$ adenosine receptor antagonist. Jacobson et al. (U.S. Pat. No. 4,968,672) teach targeting adenosine receptor antagonists to the brain as central stimulants, to the heart as cardiotonics, to the lung as anti-asthmatics, and to the kidney as diuretics. It is disclosed that an $A_1$ selective antagonist may be preferable as a diuretic since these antagonists do not decrease total blood flow to the kidney. However, some combination of $A_1/A_2$ antagonism may be desirable. By selecting appropriate amine congeners to be administered from the family of xanthine congeners taught having a range of $A_1/A_2$ selectivity ratios, one may vary the in vivo selectivity. Jacobson et al., U.S. Pat. No. 4,968,672. Badger et al., U.S. Pat. No. 4,772,607, disclose diallyl analogs of xanthine which act as adenosine antagonists displaying an increased affinity for adenosine $A_1$ receptors in particular. Use of these analogs as CNS stimulant cognition activators, antifibrillatory agents and bronchodilators is taught. In U.S. Pat. No. 4,783,530, Rzeszotarski et al. also disclose a number of xanthine derivatives which are potent adenosine $A_1$ receptor antagonists for use as bronchodilators and cardiotonics. However, in subsequent publications, U.S. Pat. No. 5,032,593 and U.S. Pat. No. 5,175,290, disclosing related xanthine derivatives, it is suggested that selectivity of these compounds for the adenosine $A_1$ receptor may not be responsible for their therapeutic effects. In addition, a method of treating cells having a reduced apical Cl-conductance by contacting these cells with a selective adenosine $A_1$ receptor antagonist has been disclosed as a treatment for cystic fibrosis. Pollard et al., U.S. Pat. No. 5,366,977.

Adenosine attenuates ischemia-reperfusion injury of the heart upon administration prior to ischemia or reperfusion. Ely, S W et al., *J. Thorac Cardiovasc Surg* 90:549–556, 1985; Olafsson B, et al. *Circ* 76:1135–1145, 1987; Lasley, R D, et al., *Am J Physiol* 263:H1460–H1465, 1992; Ely S W, Berne R M, *Circ* 85:893–904, 1992; Janier, M F, et al., *Am J Physiol* 264:H163–H170, 1993; Zhao, Z Q, et al. *Circ* 88:709–719, 1993. Following 90 minutes of ischemia, an intracoronary infusion of adenosine during reperfusion reduced infarct size, improved regional myocardial blood flow and ventricular function, decreased neutrophil infiltration of the ischemic zone of the myocardium and leukocyte plugging of capillaries, and was associated with preservation of endothelial cell structure. Olafsson B et al., *Circ* 76:1135–1145, 1987. The mechanisms by which adenosine attenuates the injury in the heart following ischemia and reperfusion are not completely understood. However, it has been determined that by acting on $A_1$ adenosine receptors, adenosine inhibits the release of neurotransmitter substances, produces negative inotropic and chronotropic responses in the heart, attenuates $Ca^{2+}$ overload of cells, and increases glycolytic flux. Ely S W, Berne R M, *Circ* 85:893–904, 1992; Brechler V et al., *J Biol Chem* 265:16851–16855, 1990. By acting on $A_2$ adenosine receptors, adenosine produces vasodilation, inhibits oxygen radical release from neutrophils, inhibits platelet aggregation, and decreases edema formation. Ely S W, Berne R M, *Circ* 85:893–904, 1992; Haselton F R et al., *J Appl Physiol* 74:1581–1590, 1993. Adenosine also serves as the primary substrate for ATP synthesis by the purine salvage pathway. When administered prior to ischemia, selective $A_1$ adenosine receptor agonist, R-PIA, has also been reported to attenuate ischemia-reperfusion injury in the heart. Thornton J D, et al., *Circ* 85:659–665, 1992. In addition, brief episodes of ischemia (approximately 5 to 15 minutes), also referred to as preconditioning ischemia, have been reported to attenuate ischemia-reperfusion injury in the heart. Thornton J D, et al., *Circ* 85:659–665, 1992; Lui G S, et al., *Circ* 84:350–356, 1991; Thornton J D, *Am J Physiol* 265:H504–508, 1993. However, the positive effects of adenosine and preconditioning ischemia were found to be antagonized by a selective $A_1$ receptor antagonist 8-cyclopentyl-1,3-dipropylxanthine (DPCPX) and a nonselective adenosine receptor antagonist 8-(p-sulfophenyl) theophylline (8-SPT), respectively. Lasley, R D, Mentzer, R M, *Am J Physiol* 263:H1460–H1465, 1992; Thornton JD, *Am J Physiol* 265:H504–508, 1993; Toombs C F, et al., *Circ* 86:986–994, 1992.

In contrast to the heart, adenosine has been reported to cause vasoconstriction in the kidney. $A_1$ receptor stimulation in the kidney was shown to produce primary vasoconstriction of the afferent arteriole and a decrease in glomerular filtration rate. Suzuki, F., et al., *J. Med Chem,* 35:3066–3075, 1992. Suzuki et al. found selective and potent antagonism of the $A_1$ adenosine receptor to be important in diuretic and natriuretic activities of the kidney. It has also been suggested that selective $A_1$ adenosine receptor blockade is more effective in ameliorating acute renal failure than non-selective antagonism of both the $A_1$ and $A_2$ receptors. Kellett, R. et al., *Br. J. Pharmacol.,* 98:1066–1074, 1989. However, Knight, R. J., et al., *J. Pharm Pharmacol.,* 45:979–984, 1993, showed that a selective $A_1$ adenosine antagonist could only provide protection against endotoxin-induced renal dysfunction in the rat in animals receiving a high dose of endotoxin. Coadministration of the $A_1$ selective adenosine antagonist DPCPX resulted in statistically significant attenuation of the reduction of renal blood flow and inulin clearance in animals receiving a high dose but not a low dose of endotoxin. From these results, Knight et al. concluded that adenosine does not play a major role in the pathophysiology of endotoxemic ARF.

Adenosine has also been reported to act upon adenosine $P_1$ receptors in the pulmonary vascular bed to induce vasoconstriction and vasodilation. Neely et al. *J. Pharmacol. and Exp. Therap.,* 250(1):170–176, 1989. In addition, ATP-sensitive purinoceptors are present on pulmonary arteries and veins which produce arterial and venular constriction of pulmonary vessels. Liu et al. *J. Pharmacol. Exp. Ther.* 251:1204–1210, 1989. It is believed that following ischemia and reperfusion, ectonucleotidase activity is reduced. A reduction in 5' nucleotidase activity can result in a decrease in the concentration of adenosine at $A_2$ adenosine receptors and an increase in ATP at $P_{2X}$ purinoceptors, resulting in an increase in pulmonary vascular tone and edema formation. Based upon potency profiles of structural analogues for ATP, ATP-sensitive ($P_2$) purinoceptors have been subclassified into $P_{2X}$ and $P_{2Y}$ purinoceptors. With few exceptions, $P_{2X}$ receptors are located on vascular smooth muscle cells and mediate vasoconstriction and $P_{2Y}$ receptors are located on endothelial cells and mediate vasodilation. Burnstock, G. and Kennedy, C., *Gen. Pharmac.* 16:433–440, 1985; Ralevic et al. *Br. J. Pharmacol.* 103:1108–1113, 1991. $P_{2X}$ purinoceptors are characterized by an agonist potency profile of α,β-methylene ATP (α,β-MeATP)>β,γ-methylene ATP (β,γ-MeATP)>ATP=2-methylthio ATP (2-MeSATP) and are selectively desensitized with α,β-MeATP. An agonist potency profile for $P_{2Y}$ purinoceptors is 2-MeSATP>ATP>α,β-MeATP, α,β, γ-MeATP. $P_{2Y}$ purinoceptors are antagonized by the $P_{2Y}$ receptor antagonist reactive blue 2. Hopwood, A. M. and Burnstock, G., *E. J. Pharmacol.* 136:49–54, 1987; Burnstock, G. and Warland, J. J. I., *Br. J. Pharmacol.* 90:383–391, 1987; Houston et al. *J. Pharmacol. Exp. Ther.* 241:501–506, 1987. Diadenosine pentaphosphate and hexaphosphate derivatives mimic the contractile effects of α,β-MeATP in the bladder and vas deferens and a synthetic α,ω,-adenine dinucleotide, $p^1$, $P^5$ diadenosine 5' pentaphosphate ($AP_5A$) desensitizes $P_{2X}$ receptors suggesting these compounds act on $P_{2X}$ receptors. Hoyle, C. H. V., *Gen. Pharmac.* 21:827–831, 1990; MacKenzie et al. *Br. J. Pharmacol.* 94:699–706, 1988; Stone, T. W., *E. J. Pharmacol.* 75:93–102, 1981; Hoyle, C. H. V., *E. J. Pharmacol.* 174:115–118, 1989. Pyridoxalphosphate-6-azophenyl-2', 4'-disulfonic acid (PPADS) selectively antagonized the nonadrenergic component of the neurogenic-induced and α,β-MeATP-induced contractions of rabbit vas deferens suggesting it is a selective antagonist of $P_{2X}$ purinoceptors. Lambrecht et al. *E. J. Pharmacol.* 217:217–219, 1992. Moreover, with the use of a selective radioligand for $P_{2X}$ receptors, [$^3$H]α,β-MeATP, and autoradiographic techniques, $P_{2X}$ purinoceptors have been identified in a variety of systemic blood vessels from different species. Bo, X. and Burnstock, G., *J. Vas. Res.* 30:87–101, 1993.

Further investigations have been undertaken to understand the mechanisms mediating vasoconstrictor responses to adenosine in the lung in the intact-chest, spontaneously breathing cat under conditions of controlled blood flow and constant left atrial pressure. It was found that adenosine induces vasoconstriction in the lung by acting on an adenosine $A_1$-"like" receptor. An $A_1$ selective agonist was approximately 10 to 30 times more potent than adenosine. It was also found that vasoconstriction response was dependent on formation of thromboxane $A_2$. Neely et al., *J. Pharmacol. and Exp. Therap.,* 258(3):753–761, 1991. It has also been reported that phorbol myristate acetate (PMA)-induced increases in capillary permeability in the isolated blood-perfused dog lung can be blocked by pretreatment with adenosine, which binds the adenosine $A_2$ receptors. When an $A_1$ antagonist, DPCPX, was administered to these animals before PMA introduction in the presence of adenosine, this permeability damage was prevented and the pulmonary vascular resistance remained unchanged from controls. Adkins et al., *Appl. Physiol.,* 1993, 74 (3):982–988. Adkins et al. suggest that this finding leads one to postulate that at least portions of the constriction produced with PMA challenge are mediated by activation of $A_1$ receptors as evidenced by the blocking effect of DPCPX on the PMA-induced resistance increase. However, as acknowledged by Adkins et al., further studies are required as the mechanisms behind PMA-induced lung injury are poorly understood and exogenous adenosine was present in these experiments. Also, the increase in vascular resistance may not play an important role in lung injury following endotoxin, PMA, or ischemia-reperfusion.

Ischemia-reperfusion injury of the lung occurs after lung transplantation, pulmonary thromboembolectomy or cardiopulmonary bypass. Egan T M, et al., *Lung transplantation. Curr Probl Surg* 26:675–751, 1989; Levinson R M, et al., *Am Rev Resp Dis* 134:1241–1245, 1986; Kuratani T, et al., *J Thorac Cardiovas Surg* 103:564–568, 1992. Ischemia-reperfusion injury of the lung also occurs after ischemia and reperfusion of distant organs, for example the intestines. Schmeling D J, et al., *Surg* 106:195–201, 1989. In the lung, two hours of ischemia followed by three hours of reperfusion produced structural and functional abnormalities that did not occur with ischemia alone. Murata T, et al., *Am Rev Resp Dis* 146:1048–1053, 1992; Hamvas A, et al., *J Appl Physiol* 72:621–628, 1992. Neutrophil infiltration, hemorrhage and edema formation occurred only following reperfusion. In conscious, intact-chest, spontaneously breathing rats, two hours of ischemia alone was associated with minimal structural changes. Murata T, et al., *Am Rev Resp Dis* 146:1048–1053, 1992. However, two hours of ischemia followed by reperfusion was associated with hemorrhagic necrosis of the lung, disrupted alveoli with exudate, destroyed endothelial cells which were detached from internal elastic lamina, and leukocyte accumulation. In isolated, perfused rabbit lungs, 40 minutes of ischemia (when both ventilation and perfusion were discontinued) followed by 55 minutes of reperfusion was associated with electron microscopic alterations of lung tissue, including gaps between endothelial cell tight junctions, gaps between the capillary lumen and interstitial space and edema formation. Zamora C A, et al., *J Appl Physiol* 74:224–229, 1993. Following ischemia and reperfusion of these rabbit lungs, the rise in pulmonary artery pressure and increase in wet-to-dry lung weight ratios were associated with an increase in thromboxane. These increases were markedly reduced by administration of a thromboxane receptor antagonist, SQ29548, prior to ischemia. Moreover SQ29548 reduced the alterations in endothelial cell gap junctions and interstitial edema formation on electron microscopy.

It has now been found that administration of an effective amount of an $A_1$ adenosine receptor antagonist prior to ischemia or during or after reperfusion prevents ischemia-reperfusion injury in these organs or related tissues. Administration of an effective amount of a $P_{2X}$ purinoceptor antagonist prior to ischemia can also prevent tissue injury resulting from ischemia-reperfusion. Compositions comprising an $A_1$ adenosine receptor antagonist and/or a $P_{2X}$ purinoceptor antagonist are useful in the prevention and treatment of ischemia-reperfusion injury following organ transplantation, resulting from surgical procedures, following angioplasty or thrombolytic therapy and associated with certain injuries or disease states. These compositions have also been found to be useful in preventing endotoxin-related tissue injury.

SUMMARY OF THE INVENTION

An object of the present invention is to provide a method of preventing or inhibiting ischemia-reperfusion organ injury comprising administering to an animal an effective amount of an $A_1$ adenosine receptor antagonist.

Another object of the invention is to provide compositions comprising an $A_1$ adenosine receptor antagonist useful in the prevention or treatment of ischemia-reperfusion organ injury resulting from transplantation, surgical procedures, angioplasty or thrombolytic therapy, or certain disease states.

Another object of the present invention is to provide a method of preventing or inhibiting ischemia-reperfusion organ injury comprising administering to an animal an effective amount of a $P_{2X}$ purinoceptor antagonist.

Another object of the present invention is to provide a method of inhibiting endotoxin-related tissue injury which comprises administering to an animal an effective amount of an $A_1$ adenosine receptor antagonist.

Another object of the present invention is to provide a method of inhibiting endotoxin-related tissue injury which comprises administering to an animal an effective amount of a $P_{2X}$ purinoceptor antagonist.

DETAILED DESCRIPTION OF THE INVENTION

ATP, which is released during ischemia, is metabolized to adenosine by species-specific ectonucleotidases located on endothelial and vascular smooth muscle cells. ATP and adenosine act on specific extracellular receptors, adenosine-sensitive $P_1$ and ATP-sensitive $P_2$ purinoceptors located on a number of cell types including endothelial and vascular smooth muscle cells, neutrophils, and platelets. These cells are important in the pathophysiology of ischemia-reperfusion injury of organs. A number of complex events occur after ischemia and reperfusion, including the release of cytokines and chemoattractants, activation of neutrophils, adherence of neutrophils to endothelial cells, and the release of oxygen radicals and vasoactive substances, including thromboxane. Following ischemia and reperfusion of the rabbit lung, an increase in thromboxane is associated with an increase in pulmonary vascular tone, alterations in endothelial cell tight junctions and pulmonary edema formation. Zamora C A, et al., *J Appl Physiol* 74:224–229, 1993. Adenosine, via its effects on specific adenosine receptors $A_1$ and $A_2$, effects pulmonary vascular tone, Neely C F, et al., *J. Pharmacol Exp Ther* 250(1):170–176, 1989; platelet function, Hourani S M O, Cusack N.J., *Actions and Structure Activity Relationships of Purines on Platelets. In Purines. Pharmacology and Physiological Roles*. Edited by T W Stone, V C H, London, pp 163–173, 1985; and superoxide anion release from neutrophils Cronstein B N, et al., *Ann NY Acad Sci* 451:291–301, 1985. Also, in isolated, blood perfused dog lungs, adenosine was found to attenuate the pulmonary edema following phorbol myristate acetate induced lung injury by acting on $A_2$ adenosine receptors. Adkins et al., *Appl. Physiol.* 74(3):982–988, 1993.

Adenosine produces vasoconstriction in the feline lung vasculature by acting on $A_1$ adenosine receptors which induce the release of thromboxane. Neely C F, et al., *J Pharmacol Exp Ther* 258:753–761, 1991. By acting on $A_2$ adenosine receptors, adenosine produces vasodilation, inhibition of oxygen radical release from neutrophils and platelet aggregation, and a decrease in endothelial cell permeability.

Adenosine-sensitive $A_1$ and $A_2$ receptors play important roles in ischemia-reperfusion injury of organs following transplantation, during certain surgical procedures, following angioplasty and thrombolytic therapy, and following shock or trauma. Adenosine, selective $A_1$ adenosine receptor agonists (when administered prior to ischemia), and brief periods of ischemia (preconditioning ischemia) have been shown to attenuate ischemia-reperfusion injury of the heart.

Such treatments are also believed to attenuate ischemia-reperfusion injury of the lung. For example, in lung transplant operations, it is possible for a surgeon to subject a lung to brief periods of ischemia prior to removing the lung from a donor. However, the effects of preconditioning are brief. A more effective treatment would be to administer a drug into the lung which would stay in the lung until transplantation takes place. As $A_1$ adenosine receptors mediate the effects of preconditioning, it has been proposed that administration of a very hydrophobic $A_1$ adenosine receptor agonist such as R-PIA could prove useful in improving the outcome of organ function following transplantation. However, administration of an $A_1$ adenosine receptor agonist can result in several unwanted side effects, including decreased heart rate and myocardial contractility, bronchospasm and a decrease in urine output resulting from decreased kidney function. It has now been found that administering a selective $A_1$ adenosine receptor antagonist attenuates ischemia-reperfusion injury more effectively and without the unwanted side effects.

In the present invention, a method of preventing ischemia-reperfusion organ injury is provided wherein an animal, preferably a human, is administered an effective amount of a selective $A_1$ adenosine receptor antagonist at a selected time prior to a surgical procedure in which ischemia is expected to occur so that the organ injury is prevented. The term "effective amount" refers to a concentration of a selective $A_1$ adenosine receptor antagonist which is sufficient to interfere with the action of adenosine upon this receptor. The term "selected time" refers to an amount of time which is sufficient to allow a selective adenosine $A_1$ receptor antagonist to bind to the adenosine $A_1$ receptors in the organ so that injury resulting from ischemia-reperfusion is decreased. It is preferred that the selected time be prior to ischemia. For example, if the adenosine $A_1$ receptor antagonist is administered to the organ directly, the preferred selected time is from about 20 to 30 minutes, more preferably 30 minutes, prior to ischemia. If the antagonist is administered intravenously, the selected time may be longer, for example, 30 minutes to an hour prior to ischemia. Surgical procedures for which this method is useful include harvesting donor organs for transplantation. Other examples of surgical procedures and organs at risk of ischemia reperfusion injury during these procedures include, but are not limited, brain injury during carotid artery surgery, cerebral vascular surgery and surgery of the heart and aorta; brain, spinal cord, intestine and kidney injury during surgery of the thoracic aorta and kidney injury during abdominal aortic surgery; lung injury following thromboembolectomy or the use of cardiopulmonary bypass during lung and heart surgery; heart injury following revascularization (coronary artery bypass graft surgery); kidney injury following surgery on renal arteries; intestinal injury following surgery on the mesenteric arteries; and skin injury following harvesting of a skin graft. While it is preferred that the $A_1$ adenosine receptor antagonist be administered prior to the surgical procedure, administration of the $A_1$ adenosine receptor antagonist after the onset of ischemia but prior to or during reperfusion has also been found to inhibit tissue injury related to ischemia-reperfusion.

Selective $A_1$ adenosine receptor antagonists can also be administered prior to or following angioplasty or thrombolytic therapy to prevent or inhibit tissue or organ injury caused by ischemia followed by reperfusion. In this method, an effective amount of an $A_1$ adenosine receptor antagonist is administered to a patient at a selected time prior to or following an angioplasty procedure or prior to or following administration of a thrombolytic agent such as urokinase so that, upon lysis of the clot, tissue injury related to ischemia followed by reperfusion is prevented.

$P_{2X}$ purinoceptors have also been identified on large and small pulmonary arteries and large pulmonary veins. During ischemia-reperfusion injury, it is believed that ectonucleotidase activity is reduced resulting in an increase in ATP at the $P_{2X}$ purinoceptors. This increase has been associated with an increase in vascular tone and edema formation. It has now been found that antagonists of $P_{2X}$ purinoceptors, such as PPADS, selectively antagonize the vasoconstrictive responses of the $P_{2X}$ receptors to selective $P_{2X}$ purinoceptor agonists such as $\alpha,\beta$-MeATP, at low, baseline pulmonary vascular tone. Such antagonists had no effect on the vasodilator response of adenosine, ATP or the selective $P_{2Y}$ purinoceptor agonist 2-MeSATP at elevated pulmonary vascular tone. Accordingly, it is believed that administration of an effective amount $P_{2X}$ purinoceptor antagonist administered at a selected time prior to, during, or following a surgical procedure in which ischemia is expected to occur can also be administered to prevent ischemia-reperfusion injury. By "effective amount" it is meant a concentration of a $P_{2X}$ purinoceptor antagonist sufficient to inhibit the vasoconstrictive response of the $P_{2X}$ receptor. By "selected time" it is meant as time which is sufficient to allow a $P_{2X}$ purinoceptor to bind to the $P_{2X}$ purinoceptor in the tissue or organ so that tissue injury relating to ischemia-reperfusion is decreased. These antagonists can also be administered prior to or following angioplasty or thrombolytic therapy to prevent ischemia-reperfusion injury related to these procedures.

In addition, it is believed that coadministration of a selective $A_1$ adenosine receptor antagonist and a $P_{2X}$ purinoceptor antagonist may also be useful in preventing or treating ischemia-reperfusion injury. A single compound which antagonizes both the $A_1$ adenosine receptor and the $P_{2X}$ purinoceptor may also be used.

Methods of the present invention are also useful in treating ischemia-reperfusion organ injury in high risk patients. Injuries or conditions such as bowel ischemia and reperfusion, sepsis, anaphylaxis, hemorrhagic shock and trauma can result in ischemia-reperfusion organ injury. Ischemia-reperfusion injury of the organs is also associated with vasculitis and autoimmune disease. In addition, cerebral air embolisms which can occur following diving and decompression are associated with ischemia-reperfusion injury of the brain. Also, following in utero fetal distress and birth, the brain of newborns may be at risk of ischemia reperfusion. For purposes of this application, patients suffering from such injuries or conditions are defined as "high risk" patients.

In addition, it is believed that the methods of the present invention are useful in preventing the nephropathy, retinopathy and neuropathy of diabetes which is secondary to ischemia-reperfusion injury.

The intact-chest spontaneously breathing cat animal model has been used to create ischemia-reperfusion injury of the lung which is morphometrically similar to this injury in other species and reproducible quantitatively. With the use of fluoroscopy, catheters are placed in the left lower lobe artery and vein in the lungs of intact-chest, spontaneously breathing cats. The lobar artery catheter is of the type which allows for isolation of the left lower lobe, preferably the catheter is a triple lumen catheter with a proximal balloon.

Normally, the left lower lobe is perfused with blood withdrawn from the aorta at a constant flow rate with the use of a peristaltic pump. However, blood flow can be stopped for a given period of time by stopping the pump. Also, with the use of fluoroscopy and a bronchial blocker, ventilation to the left lower lobe can be interrupted for the same period of time while blood flow is stopped. Ventilation and blood flow are interrupted for a period of time and then resumed. Lung injury following these periods of ischemia and reperfusion is characterized by the presence of leukocytes, red blood cells, macrophages and edema in the alveoli, as compared to controls. The morphological changes produced by two hours of ischemia followed by two hours of reperfusion were similar to those described by others in other species, including rats, rabbits and dogs. Zamora C A, et al., *J Appl Physiol* 74:224–229, 1993; Murata T, et al., *Am Rev Resp Dis* 146:1048–1053, 1992; Hamvas A, et al., *J Appl Physiol* 72:621–628, 1992.

Using this model, it has now been found that selective $A_1$ adenosine receptor antagonists administered prior to the period of ischemia and during reperfusion markedly attenuate the alveolar injury resulting from ischemia followed by reperfusion. The term "selective $A_1$ adenosine receptor antagonist" refers to antagonists which bind preferentially to the $A_1$ adenosine receptor and do not affect the $A_2$ adenosine receptor. Examples of antagonists selective for $A_1$ adenosine receptors include, but are not limited to, alkyl xanthines such as 8-cyclopentyl-1,3-dipropylxanthine (DPCPX), xanthine amine cogener (XAC), xanthine carboxylic cogener (XCC), 1,3-dipropyl-8-(3-noradamantyl) xanthine (KW 3902), 1,3-dipropyl-8-(dicyclopropylmethyl)xanthine (KF 15372), 1,3-dipropyl-8-(3-oxocyclopentyl xanthine (KFM 19), 1-propyl-3-(4-amino-3-iodophenethyl)-8-cyclopentylxanthine (BW-A844U), 1,3-dipropyl-8-sulfophenylxanthine (DPSPX), cyclopentyl theophilline (CPT) and 7-[2-ethyl(2-hydroxyethyl)amino]-ethyl]-3,7-dihydro-1,3-dimethyl-8-(phenylmethyl)-1H-purine-2,6-dione (Bamifylline (BAM)); $N^6$, 9-methyl adenines such as (±)-$N^6$-endonorbornan-2-yl-9-methyladenine (N-0861); $N^6$, 9-disubstituted adenines; 2-phenyl-7-deazaadenines such as (R)-7,8-dimethyl-2-phenyl-9-(1-phenylethyl)-7-deazaadenine; 7,8-dihydro-8-ethyl-2-(3-noradamantyl)-4-propyl-1H-imidazo[2,1-i]purin-5(4H)-one;(±)R-1-[(ϵ)-3[2-[phenylpyrazolo(1,5-a) pyridin-3-yl]acryloyl]-2-piperidine ethanol; and 8-azaxanthines such as 7-cyclopentyl-1,3-dipropyl-8-azaxanthine. Antibodies raised against the $A_1$ adenosine receptor which selectively target and bind to this receptor can also be used as $A_1$ adenosine receptor antagonists. Such antibodies targeted to the $A_1$ adenosine receptor can be produced routinely in accordance with well known methods of antibody production. It was also found that $P_{2X}$ purinoceptor antagonists administered prior to the period of ischemia markedly attenuate the alveolar injury resulting from ischemia followed by reperfusion. An example of a selective $P_{2X}$ purinoceptor antagonists is PPADS. Additional specific pharmacological antagonists of purinoceptors have been described by Humphrey PPA, et al. *Naunyn-Schmied. Arch. Pharmacol.* 352:585–596, 1995; Abbracchio M P and Burnstock G, *Pharmac. Ther.* 64:445–475, 1994; Bultmann R. et al. *Naunyn-Schmied. Arch. Pharmacol.* 354:481–490, 1996; and Bultmann R, et al. *Naunyn-Schmied. Arch. Pharmacol.* 354:498–504, 1996. Antibodies raised against the $P_{2X}$ purinoceptor which selectively target and bind to this receptor can also be used as selective $P_{2X}$ purinoceptor antagonists. Such antibodies targeted to the $P_{2X}$ purinoceptor can be produced routinely in accordance with well known methods of antibody production.

Lung pathology in ischemia-reperfusion injury animals included alveolar and perivascular edema, margination of PMNs along the venular endothelium, and alveolar infiltration of neutrophils, macrophages, and red blood cells. These parameters were reduced in a highly significant manner to control levels by intralobar infusion of XAC into the lower left lobe prior to ischemia and reperfusion, by intravenous DPCPX administration prior to ischemia or after 2 hours of ischemia and 1 hour of reperfusion, by intravenous BAM administration prior to ischemia and by intravenous PPADS administration prior to ischemia. All of the $A_1$ adenosine receptor antagonists and the $P_{2X}$ purinoceptor antagonist tested were highly effective in preventing alveolar injury. Moreover, indicators of lung injury were higher following 2 hours of ischemia and 2 hours of reperfusion than all groups, except for the number of red blood cells per alveolus and percent alveoli with edema that were similar to the 2 hours of ischemia and one hour reperfusion group. The alveolar injury following 2 hours of ischemia and 1 hour of reperfusion is milder than that following 2 hours of ischemia and 2 hours of reperfusion and is similar to that following preconditioning ischemia. Also, it was found that blocking $A_1$ adenosine receptors 1 hour after reperfusion prevented progression of all other injury parameters past the 1 hour reperfusion level. Results from electron microscopy verified the morphometric observations and clearly identifying histopathological changes in the 2 hour ischemia-2 hour reperfusion group such as interstitial edema of alveolar parenchyma including thickening of alveolar septae, endothelial cell and type I cell swelling and damage, and ruptured blood-air barriers resulting in interstitial and alveolar hemorrhage. In contrast, lung parenchyma from animals treated with an $A_1$ adenosine receptor antagonist could not be distinguished from the control lungs and the alveolar capillary endothelium and type I cell lining appeared generally normal and did not differ from perfused control lungs that showed no signs of alveolar injury.

It has also been found that compositions comprising a selective $A_1$ adenosine receptor antagonist and/or $P_{2X}$ purinoceptor antagonist are effective in preventing tissue injury related to endotoxin. Endotoxin produces organ damage directly by inducing the release of cytotoxic substances including nitric oxide and thromboxane from cells, such as endothelial cells. Endotoxin produces organ damage indirectly by inducing the release of cytotoxic substances from circulating and resident cells, including macrophages, which act locally to produce organ damage or as blood borne substances which induce distal organ damage. Endotoxin also induces the release of mediators such as nitric oxide and prostaglandins which can produce a profound shock state and organ hypoperfusion. Mayeux P R, *J. Tox. and Environ. Health* 51:415–435, 1997. Endotoxin induces tissue injury or dysfunction in a number of organs or tissues including, but not limited to, the lung, heart, eye, intestines, peritoneum, liver, stomach, ear, blood vessels, nerves, skin, brain and spinal cord, sinus and nose, kidney, testis and epididymis, ovary, fallopian tube, prostate, placenta, bronchi, and gum tissue. See, e.g., Lew W Y, et al., *Am. J. Physiol.* 272:H2989–H2993, 1997; Goddard C M, et al., *Am. J. Physiol.* 270:H1446–H1452, 1996; Behar-Cohen F F, et al., *Exp. Eye Res.* 65:533–545, 1997; Unno N, et al., *Gastroenterology* 113:1246–1257, 1997; Vos T A, et al., *Gastroenterology* 113:1323–1333, 1997; Abel-Aziz M T et al., *J. Clin. Biochem. Nutr.* 22:19–29, 1997; Sakagami T, et al., *Infection and Immunity* 65:3310–3316, 1997; Sugiura Y, et al., *Acta Otolaryngol.* 531:21–33, 1997; McKenna T M, *J. Clin. Invest.* 86:160–168, 1990. Moreover, endotoxin enhances organ injury associated with certain toxins, alcohol, parasitic infections, and ischemia and reperfusion. Vogt B A, et al., *Lab. Invest.* 72:474–483, 1995; Arai M, et al., *Jap. J. Gastroenterology* 86:1089–1095, 1989; Abel-Aziz M T, et al.,*J. Clin. Biochem. Nutr.* 22:19–29, 1997; Liu P, et al., *Circ. Shock* 43:9–17, 1994. Levels of endotoxin in amniotic fluid have also been correlated with the incidence of premature rupture of membranes in pregnancy. Hazan Y, et al., *Acta Obstet. Gynecol. Scand.* 74:275–280, 1995. Levels of endotoxin in the blood of postoperative patients have been correlated with the incidence of respiratory and renal complications. Berger D, et al., *E. Surg. Res.* 28:130–139, 1996. Levels of endotoxin in house dust of asthmatics correlate with the severity of asthma. Michel O, et al., *Am. J. Resp. Crit. Care Med.* 154:1641–1646, 1996. Levels of endotoxin in the stool of neonates with necrotizing enterocolitis correlate with the severity of bowel mucosal disease. Duffy L C, et al. *Digestive Dis. and Sci.* 42:359–365, 1997. Levels of endotoxin in the urine correlate with the presence of gram negative infection. Hurley J C and Tosolini FA, *J. Microbiol. Methods* 16:91–99, 1992. Levels of endotoxin in the culture media for in vitro fertilizations correlate with the survival of the embryo. Nagatta Y and Shirakawa K, *Fertility and Sterility* 65:614–619, 1996. Finally, levels of endotoxin in the peritoneal fluid of continuous ambulatory peritoneal dialysis (CAPD) patients has 100% sensitivity and specificity for the diagnosis of gram negative peritonitis. Ishizaki M, et al., *Advances in Peritoneal Dialysis* 12:199–202,1996. In addition, the vasculitis associated with autoimmune diseases and endothelial proliferation associated with diabetic organ injury can produce ischemia-reperfusion organ injury. Hypoxia (reduced oxygen tension) and ischemia (reduced oxygen delivery to an organ) also sensitizes tissue to the effect of endotoxin. Herbert J M, et al. *J. Cellular Physiol.* 169:290–299, 1996.

In the lung, endotoxin produces a transient rise in pulmonary artery pressure within 30–60 minutes, pulmonary capillary leak associated with ultrastructural changes in pulmonary capillary endothelial cells and microthrombosis by 60 minutes and a late pulmonary hypertension which lasts for several hours. The mechanisms of these pathophysiological changes in the lung following endotoxin are not completely understood. The acute, transient rise in pulmonary artery pressure following endotoxin is associated with increased lymph and blood levels of thromboxane and can be attenuated with cyclooxygenase inhibitors, thromboxane synthesis inhibitors and thromboxane receptor antagonists. Moreover, in the cat endotoxin produced acute pulmonary hypertension which was attenuated by cyclooxygenase inhibition. Lung pathology in endotoxin-induced injury included perivascular and peribronchial edema and hemorrhage, thickened alveolar septae, margination of neutrophils along the venular endothelium, alveolar infiltration of neutrophils and macrophages, and alveolar hemorrhagic necrosis. In other organs, similar effects of endotoxin to those described in the lung have been observed including: inflammatory cellular infiltration in the heart, stomach, liver, and ear; edema formation in the intestine and heart; leakage of red blood cells into the epithelium and submucosa in the middle ear; and cytoplasmic protuberances of ciliated cells of the inner ear.

Presently treatment of endotoxin induced organ injury includes the use of antibiotics, steroids, and antiinflammatory treatments, including nonsteroidal antiinflammatory drugs. However, the use of $A_1$ adenosine receptor antagonists, $P_{2X}$ purinoceptor antagonists, or a combination of $A_1$ and $P_{2X}$ purinoceptor antagonists alone or in combination with these treatments has now been found to provide an effective form of treatment for the prevention and/or early treatment of endotoxin-induced tissue injury.

For example, pretreatment with a composition comprising a selective $A_1$ adenosine receptor antagonist and/or $P_{2X}$ purinoceptor was found to significantly reduce the percent of alveoli injured (defined as the presence of two or more inflammatory cells or red blood cells, or edematous fluid) following administration of endotoxin in cats. Parameters relating to endotoxin injury were reduced in a highly significant manner to control levels by intravenous DPCPX administration prior to endotoxin administration, by intravenous infusion of BAM prior to and throughout endotoxin administration, and by intravenous PPADS administration prior to endotoxin administration. Coadministration of the $A_1$ adenosine receptor antagonist, BAM, and the $P_{2X}$ purinoceptor antagonist, PPADS, is also useful in protecting the tissue from injury. Compounds selective for both the $A_1$ adenosine receptor antagonist and the $P_{2X}$ purinoceptor antagonists can also be used.

Electron microscopical results show thickening of alveolar septae in lungs of endotoxin treated cats due to interstitial edema and cellular infiltration. There was transmigration of red blood cells across the blood-air barrier and their phagocytosis by alveolar macrophages. Furthermore, endothelial adhesion and digestion of the endothelial plasmalemma by granulocytes, predominantly neutrophils, was observed indicating the process of diapedesis toward the alveolar lumen, whereas granulocytes in alveolar capillaries of control cats did not show evidence of endothelial adhesion and digestion. The endotoxin-induced pathology was prevented at the EM level by pretreatment with a composition comprising an $A_1$ adenosine receptor antagonist and/or a $P_{2X}$ purinoceptor antagonist; these lungs could not be distinguished from normal controls. In addition, alveolar type II cells (alveolar septal cells) of endotoxin treated cats sported increased numbers of tall, distinct microvilli and some type II cells protruded into the alveolar lumen from a pedunculated attachment. These changes in type II cells were not observed in treated animals or controls.

The ability of these compositions to inhibit endotoxin-mediated cytotoxicity of other organs or tissues can be routinely determined in similar fashion in cell culture assays. For example, to assess the ability of compositions comprising an $A_1$ adenosine receptor antagonist and/or $P_{2X}$ purinoceptor antagonist to inhibit endotoxin mediated cytotoxicity of skin epithelial cells, skin epithelial cells can be grown in culture, exposed to compositions of the present invention and then challenged with endotoxin.

In the present invention compositions are also provided which are useful in the prevention and/or treatment of organ injury in an animal, preferably a human, resulting from ischemia followed by reperfusion. Such compositions comprise either a selective adenosine $A_1$ receptor antagonist, preferably XAC, DPCPX, bamifylline or N-0861, or a $P_{2X}$ purinoceptor antagonist such as PPADS. It is preferred that these compositions be administered prior to ischemia, preferably 30 minutes prior to ischemia. However, compositions may be administered after ischemia but prior to or during reperfusion if required due to the condition causing the injury. It is preferred that these compositions be administered by intravenous bolus injection or infusion directly to the organ. Such compositions may further comprise a pharmaceutically acceptable carrier. Pharmaceutically acceptable carriers include, but are not limited to, saline, water or dextrose and water, cyclodextrins or similar sugar solutions and low dose sodium hydroxide (approximately 0.2 N) solutions.

These compositions are also useful in inhibiting tissue injury relating to thromboxane release. Thromboxane is an important mediator of anaphylaxis and the reaction to protamine treatment (used to reverse the effect of heparin in cardiac catheterization laboratories and operating rooms). Thromboxane is also an important mediator of acute renal failure. Accordingly, $A_1$ adenosine receptor antagonists may also be useful in the prevention of contrast dye or drug induced acute renal failure. Further, different forms of acute lung injury are associated with thromboxane release. Thus, $A_1$ adenosine receptor antagonists may also be beneficial for the prevention and early treatment of acute lung injury following aspiration or smoke inhalation or associated with cerebral hemorrhage, air embolism, pancreatitis, amniotic fluid embolism, near drowning, ionizing radiation, multiple transfusions, and bacterial, viral, fungal, mycobacterial, mycoplasmal, and pneumocystic pneumonias. Also $A_1$ adenosine receptor antagonists may be beneficial for the prevention and early treatment of acute lung injury associated with certain drugs, including, but not limited to, cancer therapies such as bleomycin and mitomycin C; antibiotics such as nitrofurantoin and sulfa drugs; antiinflammatory agents such as aspirin, methotrexate and nonsteroidal anti-inflammatory agents; cardiac medications such as amiodarone, procaineamide and tocainide; and narcotics such as heroine, methadone, morphine and propoxyphene. Lung toxicity caused by other agents such as oxygen and tocolytics may also be prevented by administration of an $A_1$ adenosine receptor antagonist in accordance with the present invention.

The following non-limiting examples are provided for illustrative purposes only.

EXAMPLES

Example 1

Ischemia-reperfusion Model

The cats are anesthetized with pentobarbital sodium, 10 mg/kg, IV, and are strapped in the supine position to a fluoroscopic table. The cats spontaneously breathe room air enriched with oxygen through a cuffed endotracheal tube. A specially designed 6F triple lumen balloon perfusion catheter is passed, under fluoroscopic guidance, from an external jugular vein into the arterial branch to the left lower lung lobe. After the lobar artery is vascularly isolated by distension of the balloon cuff on the catheter and the cat is heparinized (1000 U/kg, IV), the lobe is perfused with blood withdrawn from the femoral artery through the catheter lumen immediately beyond the balloon cuff. Perfusion pressure in the lobar artery is measured through the third lumen, 5 mm distal to the perfusion port. The lobe is perfused with a Harvard model 1210 peristaltic pump, and the perfusion rate is adjusted so that arterial pressure in the perfused lobe approximates mean pressure in the main pulmonary artery and is not changed during an experiment. Flow rates in the left lower lobe range from 35–45 ml/min. Left atrial pressure is measured with a transseptally placed double lumen catheter. Aortic pressure is measured with a catheter, inserted into the aorta by way of a femoral artery. All vascular pressures are measured with Gould transducers zeroed at right atrial level, and mean pressures, obtained by electronic integration, are recorded on a Gould recorder.

Following catheter placements, the animals are allowed to recover for one hour. During the ischemia period, the Harvard peristaltic pump is stopped and the circuit is attached to the femoral vein catheter. The femoral vein is perfused at 35 ml/min with the Harvard peristaltic pump during the period of ischemia with blood withdrawn from the aorta which normally perfuses the left lower lobe. Also, with the use of fluoroscopy a 4F bronchial blocker is inserted into the left lower lobe bronchus and a balloon is distended with contrast dye. Ventilation to the left lower lobe is blocked during the period of ischemia. After the ischemic interval of two hours, the left lower lobe is perfused for two hours at a rate of 35 ml/min with the use of the Harvard peristaltic pump with blood withdrawn from the aorta and the bronchial blocker is removed.

Example 2

Characterization of Lung Injury

Following two hours of ischemia (when there is no blood flow or ventilation to the left lower lobe) and one (Group II, n=5) or two hours (Group I, n=5) of reperfusion, the ischemia-reperfusion injury in the cats was quantitated using light microscopy. During two hours of ischemia followed by one or two hours of reperfusion the animals were stable. Indicators of lung injury were higher following two hours of ischemia and 2 hours of reperfusion as compared to the injury observed following two hours of ischemia and 1 hour of reperfusion. Lung injury was characterized by a significant increase in percent of injured alveoli as evidenced by the presence of leukocytes, red blood cells, macrophages and edema, as compared with control animals undergoing two hours of perfusion only. These morphological changes produced by two hours of ischemia followed by two hours of reperfusion were similar to those described by others in other species, including rats, rabbits and dogs.

Example 3

Inhibition of Ischemia-reperfusion Injury in the Lung

Separate groups of cats received either the selective $A_1$ adenosine receptor antagonist xanthine amine congener (XAC), 1,3 dipropyl 8-cyclopentylxanthine (DPCPX) or bamifylline (BAM) or the $P_{2X}$ purinoceptor antagonist pyridoxalphosphate-6-azophenyl-2',4'-disulfonic acid (PPADS). XAC (0.075 mg/kg/hr, Group III, n=7) was infused into the intralobar artery (i.a.) starting 30 minutes prior to ischemia and continued for 30 minutes. DPCPX (6 mg/kg) was administered as an intravenous (i.v.) bolus either 30 minutes before ischemia (Group IV, n=5) or 1 hour after reperfusion (Group V, n=6). BAM (10 mg/kg, Group VI, n=5) was administered as an i.v. bolus 30 minutes before ischemia. PPADS (15 mg/kg, Group VII, n=3) was administered as an i.v. bolus 30 minutes before ischemia. Control animals (Group VIII, n=5) were perfused for 2 hours.

During ischemia and reperfusion, on-line measurements of mean lobar arterial, femoral arterial, and left atrial pressures were obtained. Arterial blood gases were obtained prior to ischemia (baseline), following 1 and 2 hours of ischemia, and following 1 and 2 hours of reperfusion. These data were analyzed with the use of Student's t-test for paired analysis with Bonferroni correction for multiple comparisons within groups and ANOVA with Bonferroni correction for multiple comparison between groups. Group means were considered statistically significant at $p<0.05$.

At the end of the reperfusion period, the cats received an overdose of pentobarbital (25 mg/kg) and the lower left lobar was perfusion fixed in situ with 4% formalin (3 to 4 minutes) while lungs were inflated to a normal end expiratory pressure of 15 cm $H_2O$. Eight random tissue cubes were immersion fixed in formalin and Bouin's fixative. Paraffin sections, 5 $\mu M$ in thickness and stained with hematoxylin and eosin, were analyzed for lung injury with a double blind system using the following parameters: percent alveoli containing one or more neutrophils (PMNs), macrophages, or red blood cells (RBCs) (% alv); average number of each cell type per 100 alveoli (#/alv), percent alveoli containing edematous fluid (edematous alveoli (%)) and percent injured alveoli containing two or more inflammatory cells or RBCs, or edematous fluid (injured alveoli (%)). These parameters were based on 540 alveoli per cat, randomly selected in groups of 8 per field using 40X objective. Percentage data for each cat are arcsin transformed and group means were analyzed statistically using ANOVA and Bonferroni range test. The level of significance was set at p<0.05. Data are provided in Table 1.

(Group III, n=5). PPADS was administered at 15 mg/kg as an intravenous bolus 30 minutes before administration of the endotoxin (Group IV, n=3). In addition, a combination of PPADS (15 mg/kg, i.v. prior to endotoxin administration) and BAM (10 mg/kg/hr, continuous intravenous infusion 30 minutes prior to and throughout endotoxin until 1 hour post endotoxin) was administered (Group V, n=3). *E. coli* endotoxin (Sigma Chemical Com., St. Louis, Mo.) was dissolved in 0.9% saline at 2.5 mg/ml. The endotoxin (15 mg/kg) was administered to treated groups and to a group of untreated cats (Group I, n=5) as a continuous intralobar infusion over

TABLE 1

Effects of $A_1$ adenosine receptor and $P_{2X}$ purinoceptor antagonists on alveolar inflammatory cells, red blood cells and edema in cat lung after ischemia-reperfusion

| Treatment groups | | PMN % alv | PMN #alv | Macro % alv | Macro #alv | RBC % alv | RBC #alv | Edematous alveoli (%) | Injured alveoli (%) |
|---|---|---|---|---|---|---|---|---|---|
| I | Isch-reperf. (2h) (n = 5) | 22 ± 7 | 33 ± 13 | 33 ± 11 | 58 ± 23 | 39 ± 7 | 125 ± 60 | 22 ± 14 | 60 ± 10 |
| II | Isch-reperf. (1h) (n = 5) | 11 ± 4 | 14 ± 8 | 14 ± 5 | 19 ± 6 | 15 ± 7 | 60 ± 49 | 10 ± 4 | 22 ± 3 |
| III | XAC (i.a. n = 7) | 7 ± 2 | 8 ± 3 | 7 ± 2 | 9 ± 4 | 10 ± 3 | 14 ± 5 | 2 ± 3 | 7 ± 2 |
| IV | DPCPX 30 min before ischemia (i.v. n = 5) | 10 ± 6 | 14 ± 12 | 11 ± 5 | 14 ± 8 | 8 ± 4 | 25 ± 31 | 3 ± 4 | 13 ± 7 |
| V | DPCPX 1 hr after reperfusion (i.v. n = 6) | 7 ± 2 | 8 ± 2 | 9 ± 5 | 12 ± 7 | 6 ± 4 | 9 ± 6 | 0.0 | 6 ± 2 |
| VI | BAM (i.v. n = 5) | 8 ± 2 | 9 ± 2 | 7 ± 2 | 9 ± 3 | 3 ± 1 | 5 ± 3 | 0.0 | 4 ± 1 |
| VII | PPADS (i.v. n = 3) | 7 ± 0.4 | 8 ± 1 | 5 ± 2 | 6 ± 2 | 11 ± 1 | 32 ± 25 | 2 ± 2 | 8 ± 3 |
| VIII | Control (n = 5) | 5 ± 1 | 5 ± 2 | 3 ± 1 | 3 ± 1 | 8 ± 4 | 12 ± 6 | 0.0 | 5 ± 1 |

For electron microscopy (EM), representative samples of <1 mm³ size were sampled immediately from the perfusion fixed left lower lobe of all cat lungs and were post fixed in Karnovsky's fixative overnight, rinsed in cacodylate buffer, osmicated, and prepared for EM according to standard techniques using epon-araldite for embedding. Ultrathin (silver) sections were stained with uranyl acetate and lead citrate and viewed and photographed with a Phillips 110 microscope.

Example 4
Inhibition of Endotoxin-induced Lung Injury

The selective $A_1$ adenosine receptor antagonists, DPCPX and Bamifylline (BAM), were administered to cats. DPCPX was dissolved in 20 ml Molecusol® (hydroxypropyl-β cyclodextrin, Pharmatec Inc., Alachua, Fla.) plus 10 ml 0.2 N NaOH to a concentration of 3.3 mg/ml and administered at 5 mg/kg as an intravenous bolus to cats 30 minute before the administration of the endotoxin (Group II, n=5). BAM was dissolved in 0.9% saline at 2 to 4 mg/ml and administered at 10 mg/kg/hr as a continuous intravenous infusion during and for 30 minutes after the endotoxin infusion 30 to 40 minutes into the left lower lobe. In control animals (Group VI, n=5), the lower left lobe was perfused for one hour only with blood drawn from the aorta.

Hemodynamic measurements, including mean lobar arterial, femoral arterial, and left atrial pressures were obtained before endotoxin infusion (baseline), during endotoxin infusion and two hours following initiation of the endotoxin infusions. Arterial blood gases were obtained prior to endotoxin (baseline) at 15, 30 minutes, and 1 and 2 hours following the onset of the endotoxin infusion. These data were analyzed with the use of Student's t-tests for paired analysis with Bonferroni correction for multiple t-tests for comparisons within a group and ANOVA with Bonferroni correction for multiple comparisons between groups. Group means were considered statistically significant at p<0.05.

Two hours after completion of the endotoxin infusion, the cats received an overdose of pentobarbital (50 mg/kg) and the left lower lobe was perfusion fixed in situ and the lung specimens were analyzed as described in Example 3. Data are provided in Table 2.

TABLE 2

Effects of $A_1$ adenosine receptor and/or $P_{2X}$ purinoceptor antagonists an alveolar inflammatory cells, red blood cells and edema in cat lung after endotoxin

| Treatment groups | PNN % alv | PNN #alv | Macro % alv | Macro #alv | RBC % alv | RBC #alv | Edematous alveoli (%) | Injured alveoli (%) |
|---|---|---|---|---|---|---|---|---|
| I Endotoxin (15 mg/kg i.v. n = 5) | 25 ± 9 | 33 ± 14 | 26 ± 12 | 38 ± 19 | 50 ± 32 | 203 ± 124 | 22 ± 17 | 57 ± 31 |
| II DPCPX + EN (n = 5) | 9 ± 2 | 11 ± 3 | 8 ± 2 | 10 ± 2 | 9 ± 1 | 20 ± 6 | 0.6 ± 0.1 | 9 ± 1 |
| III BAM + EN (n = 5) | 8 ± 4 | 11 ± 7 | 7 ± 4 | 9 ± 5 | 14 ± 4 | 56 ± 51 | 5 ± 3 | 21 ± 14 |
| IV PPADS + EN (n = 3) | 11 ± 2 | 12 ± 2 | 10 ± 1 | 12 ± 3 | 5 ± 3 | 9 ± 5 | 1 ± 1 | 7 ± 4 |
| V EN + PPADS + BAM (n = 3) | 7 ± 4 | 8 ± 4 | 7 ± 6 | 7 ± 6 | 7 ± 5 | 17 ± 12 | 0.4 ± 0.6 | 5 ± 2 |
| VI Control (n = 5) | 5 ± 1 | 6 ± 3 | 5 ± 3 | 6 ± 4 | 8 ± 3 | 13 ± 5 | 0.0 | 4 ± 1 |

Tissue samples were also prepared for analysis by electron microscopy as described in Example 3.

Example 5
Inhibition of Ischemia-reperfusion Injury in Lungs Pretreated with N-0861

A separate group of animals will receive the selective $A_1$ adenosine receptor antagonist, $N^6$ endonorbornan-2-yl-9-methyladenine, N-0861, (2 mg/kg) as an intravenous bolus plus a continuous infusion of 0.2 mg/kg/min 30 minutes prior to ischemia and continued for 30 minutes or at the same dose one hour after reperfusion. Following reperfusion, lung specimens will be examined and results analyzed in accordance with Example 3.

Example 6
Inhibition of Endotoxin-induced Lung Injury in Lungs Pretreated with N-0861

A separate group of animals will receive the selective $A_1$ adenosine receptor antagonist, N-0861, (2 mg/kg) as an intravenous bolus plus a continuous intravenous infusion of N-0861 (0.2 mg/kg/min) for 30 minutes prior to endotoxin administration. This continuous intravenous infusion of N-0861 is continued during endotoxin administration and for 1 hour after endotoxin. Following endotoxin administration, lung specimens will be examined and results analyzed in accordance with Example 3.

Example 7
Assay for Determining Effects of $A_1$ Adenosine Receptor Antagonist and/or $P_{2X}$ Purinoceptor Antagonist in Skin Epithelial Cells Skin epithelial cells are grown in 24-well culture flasks in RPMI medium containing 10% fetal bovine serum or other suitable medium recommended by the supplier. Skin epithelial cells are labeled to approximately 1 hour at 37° C. with $^{51}$Cr (40 µCi as sodium chromate/$10^6$ cells, specific activity 456 mCi/mg Cr). The cells are then washed and allowed to leak for about 1 hour at 37° C. in RPMI plus 10% fetal bovine serum. The cells are then preincubated for 2 hours with 0.1 ml of phorbol 12-myristate 13-acetate (PMA; 1 µM). The cells are washed again with the medium to remove the PMA. The cells are then incubated with different concentrations (0.1 pg-1 µg/ml in 0.1 ml) of endotoxin in triplicate for 6 hours in the medium containing 10% fetal bovine serum and 2 U/ml adenosine deaminase. Six hours later, the uppermost 0.1 ml of supernatant is removed from the wells of the plate and counted for radioactivity in a gamma counter. The effect of an $A_1$ adenosine receptor antagonist such as 1,3-dipropyl-8-cyclopentylxanthine (DPCPX; 1 nM–10 µM) and/or a $P_{2X}$ purinoceptor antagonist such as pyridoxalphosphate-6-azophenyl-2',4' disulfonic acid (PPADS; 5–50 µM) is studied by preincubating the cells with DPCPX, PPADS or DPCPX plus PPADS for 30 to 60 minutes before challenging with endotoxin. Total releasable counts are determined by freezing and thawing of $^{51}$Cr-labeled cells in hypotonic medium. Spontaneous release is determined from the wells containing no PMA and endotoxin. Results are expressed as:

$$\% \text{ Chromium release} = \frac{\text{Experimental release} - \text{spontaneous release}}{\text{Total releasable counts} - \text{spontaneous release}} * 100$$

What is claimed is:

1. A method of preventing or treating endotoxin-related tissue injury in an animal comprising administering to an animal an effective amount of an $A_1$ adenosine receptor antagonist so that endotoxin-related tissue injury is prevented or treated.

2. The method of claim 1 further comprising administering an effective amount of a $P_{2X}$ purinoceptor antagonist.

3. The method of claim 1 further comprising administering to the animal an antibiotic, steroid, or anti-inflammatory treatment used in the treatment of endotoxin-related tissue injury.

4. The method of claim 2 further comprising administering to the animal an antibiotic, steroid, or anti-inflammatory treatment used in the treatment of endotoxin-related tissue injury.

5. A method of preventing or treating endotoxin-related tissue injury in an animal comprising administering to an animal an effective amount of a $P_{2X}$ purinoceptor antagonist so that endotoxin-related tissue injury is prevented or treated.

6. The method of claim 5 further comprising administering to the animal an antibiotic, steroid, or anti- inflammatory treatment.

* * * * *